(12) United States Patent
McCarthy (10) Patent No.: US 8,956,416 B2
(45) Date of Patent: Feb. 17, 2015

(54) VERTEBRAL OSTEOSYNTHETIS EQUIPMENT

(75) Inventor: Kevin McCarthy, Baton Rouge, LA (US)

(73) Assignee: Medicrea International, Neyron (FR)

( * ) Notice: Subject to any disclaimer, the term of this patent is extended or adjusted under 35 U.S.C. 154(b) by 533 days.

(21) Appl. No.: 13/263,751

(22) PCT Filed: Apr. 26, 2010

(86) PCT No.: PCT/IB2010/051821
§ 371 (c)(1),
(2), (4) Date: Jan. 27, 2012

(87) PCT Pub. No.: WO2010/125514
PCT Pub. Date: Nov. 4, 2010

(65) Prior Publication Data
US 2012/0172989 A1    Jul. 5, 2012

(30) Foreign Application Priority Data
Apr. 27, 2009   (FR) ..................... 09 02030

(51) Int. Cl.
*A61F 2/44*    (2006.01)
*A61F 2/46*    (2006.01)
(Continued)

(52) U.S. Cl.
CPC ............ *A61F 2/4455* (2013.01); *A61F 2/4611* (2013.01); *A61B 17/0642* (2013.01); *A61B 17/7059* (2013.01); *A61F 2/447* (2013.01); *A61F 2002/2835* (2013.01); *A61F 2002/30433* (2013.01); *A61F 2002/30507* (2013.01); *A61F 2002/30576* (2013.01); *A61F 2002/30604* (2013.01); *A61F 2002/30892* (2013.01);
(Continued)

(58) Field of Classification Search
CPC ..... A61F 2/4455; A61F 2/446; A61F 2/4611; A61F 2002/30904
USPC ......................................... 623/17.11
See application file for complete search history.

(56) References Cited

U.S. PATENT DOCUMENTS 3,532,142 A * 10/1970 Ziegler ............................ 81/456
3,695,321 A * 10/1972 Garehime, Jr. .................. 81/448
(Continued)

FOREIGN PATENT DOCUMENTS

FR        2822674       10/2002
WO    WO2007048012      4/2007

*Primary Examiner* — Ellen C Hammond
*Assistant Examiner* — Stuart S Bray
(74) *Attorney, Agent, or Firm* — Defillo & Associates, Inc; Evelyn A. Defillo (57) ABSTRACT

A vertebral osteosynthesis equipemnt including an intervertebral implant (1); a member (2) for connecting vertebral bodies (100) of both treated vertebrae intended to be assembled to the intervertebral implant (1); and a member (3) for assembling the connecting member (2) to the intervertebral implant (1). The intervertebral implant (1) includes on its proximal side relatively to the direction of its introduction into the intervertebral space (102), a hole comprising two coaxial portions, i.e. a proximal portion of larger section and a distal portion of smaller section, these proximal and distal portions comprising respective connecting means. The connecting member (2) includes a hole which allows it to be engaged onto a guiding rod (50) intended to be inserted into said distal portion (13) of the hole of the implant (1), and the assembling member (3) comprises a conduit on this guiding rod (50).

7 Claims, 4 Drawing Sheets (51) Int. Cl.
*A61B 17/064* (2006.01)
*A61B 17/70* (2006.01)
*A61F 2/28* (2006.01)
*A61F 2/30* (2006.01)

(52) U.S. Cl.
CPC .............. *A61F 2002/30904* (2013.01); *A61F 2002/4475* (2013.01); *A61F 2002/4627* (2013.01); *A61F 2002/4629* (2013.01); *A61F 2220/0025* (2013.01); *A61F 2220/0041* (2013.01)
USPC ............................................ 623/17.16

(56) References Cited

U.S. PATENT DOCUMENTS

| | | | |
|---|---|---|---|
| 3,709,089 A * | 1/1973 | Seetaram | 411/61 |
| 6,156,037 A * | 12/2000 | LeHuec et al. | 606/247 |
| 6,331,179 B1 * | 12/2001 | Freid et al. | 606/279 |
| 6,576,017 B2 * | 6/2003 | Foley et al. | 623/17.16 |
| 6,964,664 B2 * | 11/2005 | Freid et al. | 606/281 |
| 7,172,627 B2 * | 2/2007 | Fiere et al. | 623/17.11 |
| 8,142,435 B2 * | 3/2012 | Refai et al. | 606/86 A |
| 8,142,441 B2 * | 3/2012 | Refai et al. | 606/99 |
| 8,147,554 B2 * | 4/2012 | Hansell et al. | 623/17.16 |
| 8,216,312 B2 * | 7/2012 | Gray | 623/17.11 |
| 8,262,705 B2 * | 9/2012 | Bray | 606/280 |
| 8,267,997 B2 * | 9/2012 | Colleran | 623/17.11 |
| 8,343,188 B2 * | 1/2013 | Michelson | 606/246 |
| 8,343,219 B2 * | 1/2013 | Allain et al. | 623/17.11 |
| 8,343,220 B2 * | 1/2013 | Michelson | 623/17.11 |
| 8,353,913 B2 * | 1/2013 | Moskowitz et al. | 606/86 A |
| 8,353,959 B2 * | 1/2013 | Michelson | 623/17.11 |
| 8,403,986 B2 * | 3/2013 | Michelson | 623/17.11 |
| 8,430,929 B2 * | 4/2013 | Tribus | 623/17.11 |
| 8,454,694 B2 * | 6/2013 | Armstrong et al. | 623/17.11 |
| 8,480,715 B2 * | 7/2013 | Gray | 606/279 |
| 8,523,947 B2 * | 9/2013 | Theofilos | 623/17.16 |
| 8,540,769 B2 * | 9/2013 | Janowski et al. | 623/17.11 |
| 8,562,682 B2 * | 10/2013 | Gill et al. | 623/17.15 |
| 8,641,765 B2 * | 2/2014 | Muhanna | 623/17.16 |
| 2001/0020185 A1 * | 9/2001 | Ray | 623/17.11 |
| 2002/0058939 A1 * | 5/2002 | Wagner et al. | 606/61 |
| 2002/0123750 A1 | 9/2002 | Eisermann et al. | 606/69 |
| 2003/0065394 A1 * | 4/2003 | Michelson | 623/17.11 |
| 2003/0078668 A1 * | 4/2003 | Michelson | 623/17.16 |
| 2003/0135279 A1 * | 7/2003 | Michelson | 623/17.16 |
| 2003/0149482 A1 * | 8/2003 | Michelson | 623/17.11 |
| 2004/0249377 A1 * | 12/2004 | Kaes et al. | 606/61 |
| 2005/0065605 A1 * | 3/2005 | Jackson | 623/17.11 |
| 2005/0101960 A1 * | 5/2005 | Fiere et al. | 606/72 |
| 2006/0235533 A1 * | 10/2006 | Blain | 623/17.16 |
| 2008/0058932 A1 * | 3/2008 | Trieu et al. | 623/17.11 |
| 2008/0161925 A1 * | 7/2008 | Brittan et al. | 623/17.16 |
| 2008/0300634 A1 * | 12/2008 | Gray | 606/280 |
| 2009/0048677 A1 * | 2/2009 | McLeod et al. | 623/17.16 |
| 2009/0234455 A1 * | 9/2009 | Moskowitz et al. | 623/17.11 |
| 2010/0100138 A1 * | 4/2010 | Reynolds et al. | 606/86 A |
| 2010/0114317 A1 * | 5/2010 | Lambrecht et al. | 623/17.11 |
| 2011/0040382 A1 * | 2/2011 | Muhanna | 623/17.11 |
| 2011/0112587 A1 * | 5/2011 | Patel et al. | 606/86 A |
| 2011/0118840 A1 * | 5/2011 | Huntsman et al. | 623/17.11 |
| 2011/0125267 A1 * | 5/2011 | Michelson | 623/17.11 |
| 2011/0202136 A1 * | 8/2011 | Brittan et al. | 623/17.16 |
| 2011/0270318 A1 * | 11/2011 | Michelson | 606/279 |
| 2012/0010716 A1 * | 1/2012 | Spann | 623/17.16 |
| 2012/0029641 A1 * | 2/2012 | Curran et al. | 623/17.16 |
| 2012/0116520 A1 * | 5/2012 | Cauthen et al. | 623/17.16 |
| 2012/0130387 A1 * | 5/2012 | Simpson et al. | 606/104 |
| 2012/0150301 A1 * | 6/2012 | Gamache et al. | 623/17.16 |
| 2012/0209331 A1 * | 8/2012 | Michelson | 606/264 |
| 2012/0209388 A1 * | 8/2012 | Curran et al. | 623/17.16 |
| 2013/0096683 A1 * | 4/2013 | Kube, II | 623/17.16 |
| 2013/0218279 A1 * | 8/2013 | Michelson | 623/17.16 |
| 2013/0317616 A1 * | 11/2013 | Beyersdorff et al. | 623/17.15 |

* cited by examiner

VERTEBRAL OSTEOSYNTHETIS EQUIPMENT

CROSS REFERENCE TO RELATED APPLICATION

This application is a national stage entry of PCT/IB2010/051821 filed Apr. 26, 2010, under the International Convention, claiming priority over FR 0902030 filed Apr. 27, 2009.

FIELD OF THE INVENTION

The present invention relates to a piece of vertebral osteosynthesis equipment.

BACKGROUND TO THE INVENTION

The immobilization of two consecutive vertebrae by placing between these vertebrae, an implant intended to be colonized by growing bone cells so as to achieve what should be called "bone fusion" of the vertebrae, is well known. This intervertebral implant may notably be in the form of a cage in stiff material, against which the vertebrae bear, the cavity(ies) of which receive(s) a porous, bone or synthetic graft.

Associating with the intervertebral implant, a member for connecting two vertebrae externally to the intervertebral space, notably as a clamp, is also known, the respective branches of which are inserted into the bodies of both vertebrae. With this connecting member, both vertebrae may be immobilized for the time during which bone fusion is performed and the risk of expelling this implant out of this space may be prevented. It is preferable that this connecting member be connected to the intervertebral implant so that it may further be an obstacle to movements of the implant in the intervertebral space.

Such a piece of equipment is currently implanted via an anterior approach, in order to have sufficient space for being able to place the connecting member in the vertebral bodies and for achieving the assembly of this connecting member to the intervertebral implant.

This anterior approach however has the significant drawback of being strongly invasive and of making the surgical operation complicated.

Therefore there exists the need of a piece of vertebral osteosynthesis equipment as mentioned earlier, which may be placed via an approach other than a purely anterior approach, and in particular via a side approach.

SUMMARY OF THE INVENTION

The object of the present invention is to provide such a piece of equipment.

This piece of equipment comprises in a way known per se,
an intervertebral implant;
a member for connecting vertebral bodies of both treated vertebrae intended to be assembled to the intervertebral implant;
a member for assembling the connecting member to the intervertebral implant, and
instruments for placing this implant, this connecting member and this assembling member.

According to the invention, the intervertebral implant comprises on its proximal side relatively to the direction of its introduction into the intervertebral space, a hole comprising two coaxial portions, i.e. a proximal portion of larger section and a distal portion of smaller section, these proximal and distal portions comprising respective connecting means;

the connecting member comprises a hole which allows it to be engaged onto a guiding rod intended to be inserted into said distal portion of the hole of the implant;

the assembling member comprises a conduit which allows it to be engaged and closely fitted on this same guiding rod, and connecting means able to cooperate with the connecting means of the proximal portion of the hole of the implant.

By "close-fitting engagement", it should be understood that the assembling member may be engaged by sliding it on the guiding rod, but without any substantial play perpendicularly to the axis of this guiding rod.

The vertebral osteosynthesis piece of equipment according to the invention thus comprises a guiding rod intended to be connected to the implant as soon as before this implant is placed in the intervertebral space, and intended to remain in place on this implant until the end of the placement procedure, this guiding rod not being an obstacle for placing said assembling member by means of both portions of the hole which the implant comprises.

The guiding rod thus allows the assembling member to be perfectly guided and aligned with the axis of the hole of the implant.

The result is that with the piece of equipment according to the invention, the assembling of the connecting member with the implant may be carried out under the best conditions, and the placement of the assembling member is easy, which allows the use of a narrow and not very invasive approach, in particular a purely side approach.

The setting-up instruments in addition to said guiding rod, which includes connecting means able to cooperate with the connecting means of the distal portion of the hole of the implant, in order to achieve the assembling of this rod to the implant, may comprise:

an instrument for introducing and/or impacting the implant in the intervertebral space, which comprises a conduit allowing it to be fittingly engaged onto said guiding rod when this rod is connected to the implant, and which comprises a distal end capable of bearing against the implant in this engagement condition;

an instrument for creating holes in the vertebral bodies of both vertebrae, comprising a conduit which allows it to be fittingly engaged on said guiding rod when this rod is connected to the implant;

an instrument for introducing and/or impacting the connecting member, comprising a conduit which allows it to be fittingly engaged onto said guiding rod when this rod is connected to the implant, and which comprises a distal end capable, in this engagement condition, of bearing against the connecting member engaged on the guiding rod;

an instrument for introducing and placing the assembling member, which comprises a conduit allowing it to be fittingly engaged on said guiding rod when this rod is connected to the implant.

Here also, by "fittingly engaged" it should be understood that the setting-up instruments may be slidably engaged onto the guiding rod but without any substantial play perpendicularly to the axis of this guiding rod.

The procedure for placing the piece of equipment comprises the following steps:
connecting the guiding rod to the implant;
engaging onto the guiding rod the introduction and/or impaction instrument and then introducing and/or impacting the implant into the intervertebral space;
withdrawing the introduction and/or impaction instrument;

engaging onto the guiding rod the instrument for creating holes in the vertebral bodies and creating these holes by means of this instrument;

withdrawing the instrument for creating holes in the vertebral bodies;

engaging onto the guiding rod the connecting member and the instrument for introducing and/or impacting this connecting member and placing the connecting member on the vertebral bodies;

withdrawing the instrument for introducing and/or impacting the connecting member;

engaging onto the guiding rod the assembling member and the instrument for introducing and placing this assembling member and placing the assembling member in the proximal portion of the hole of the implant by means of this instrument;

withdrawing the instrument for introducing and placing the assembling member;

withdrawing the guiding rod.

With the piece of equipment according to the invention, it is thereby possible to obtain, in addition to perfect coaxiality of the assembling member with the hole of the implant, perfect parallelism of the holes made in the vertebral bodies with this same hole of the implant, and coaxiality of the hole of the connecting member with this hole of the implant.

The means for connecting the guiding rod to the distal portion of the hole of the implant may comprise slightly conical forms of the distal end portion of the guiding rod and of this distal portion of the hole, preferably however, these connecting means comprise a tapped thread of said distal portion of the hole and a threading on the distal end portion of the guiding rod.

Preferably, the means for connecting the assembling member and the proximal portion of the hole of the implant comprise a tapped thread of said proximal portion of the hole and a threading of the assembling member.

Advantageously, in this case, the connecting member comprises, at its hole, allowing this connecting member to be engaged onto the guiding rod, a tapped portion through which the assembling member should be screwed in order to be able to be then screwed into said proximal portion of the hole of the implant.

In the case when the assembling member would unscrew from the hole of the implant until it emerges from this hole, said tapped portion of the connecting member would allow this assembling member to be retained on the connecting member.

The implant advantageously comprises at least one cavity for receiving a porous graft intended to be invaded by growing bone cells. Preferably, in this case, the implant comprises a wall parallel to the direction of its introduction into the intervertebral space, in which the aforementioned hole of this implant is made.

This wall creates an area of sufficient thickness for creating this hole and allows longitudinal reinforcement of the implant, making the latter able to support without any risk of deterioration the stresses generated by its introduction and/or its impaction into the intervertebral space.

According to a preferred embodiment of the piece of equipment, in this case, said wall is extended on the distal side, with two walls diverging from each other, these divergent walls being connected to two opposite peripheral walls of the implant.

With this shape, the impaction forces may be perfectly distributed over the whole of the structure of the implant. The two divergent walls further allow delimitation with the peripheral walls of the implant of a distal cavity of large size, able to receive a graft having an extending contact surface with the bone tissues of the vertebrae.

Preferably, the connecting member and the instrument for introduction and/or impacting this connecting member comprise connecting means allowing this connecting member and this instrument to be bound with each other in rotation about the axis of the hole which the connecting member comprises and of the conduit which the instrument comprises.

The latter when it is engaged onto the guiding rod, enables the connecting member to be angularly oriented for the case when this would prove to be necessary in order to bring this connecting member opposite to the pierced holes in the vertebral bodies.

These connecting means may notably comprise protrusions laid out on the distal end of the instrument and corresponding cavities laid out on the connecting member.

BRIEF DESCRIPTION OF THE FIGURES

The invention will be understood and other features and advantages thereof will become apparent with reference to the appended schematic drawing, illustrating as a non-limiting example, a preferred embodiment of the piece of equipment to which it relates.

DETAILED DESCRIPTION OF THE INVENTION

The FIGS. 1-5 represent a piece of vertebral osteosynthesis equipment including an intervertebral implant 1, a member 2 for connecting the vertebral bodies 100 of two treated vertebrae, an assembling member 3 for assembling the connecting member 2 to the intervertebral implant, and FIGS. 12-16 represent instruments 50-54 for placing this implant 1, this connecting member 2 and this assembling member 3.

Figures 1, 2:
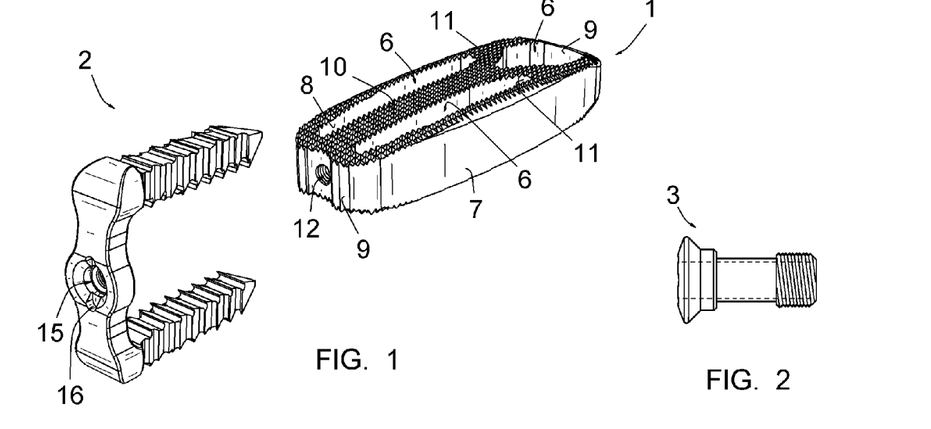
FIG. 1 is a perspective view of an intervertebral implant and of a connecting member as a clamp which this piece of equipment comprises.
FIG. 2 is a side view, at an enlarged scale, of an assembling member in the form of a screw for assembling the connecting member to the implant.
Figure 5:
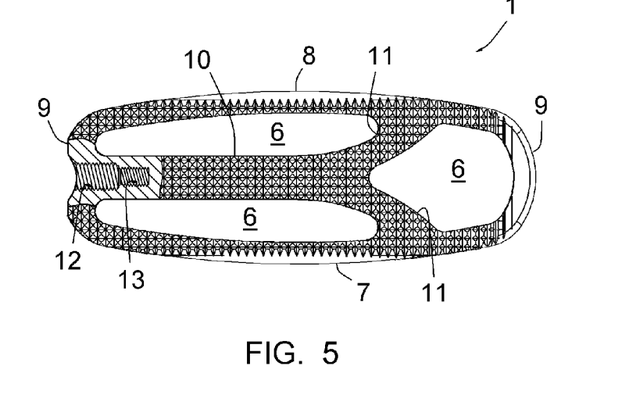
FIG. 5 is a top view of the implant, as a partial sectional view at a proximal hole which this implant comprises.

By more particularly referring to FIGS. 1 and 5, it appears that the intervertebral implant 1 is in the form of a cage delimiting cavities 6 for receiving porous, bone or synthetic grafts. These grafts are intended to be colonized by growing bone cells, so as to achieve what should be called "bone fusion" of the vertebrae.

The implant 1 is intended to be introduced into the intervertebral space to be treated via a side approach. It comprises peripheral walls, including an anterior wall 7, a posterior wall 8 and side walls 9. It also comprises internal walls, including a proximal wall 10, parallel to the direction of the direction of its introduction into the intervertebral space and positioned in a middle position relatively to the anterior wall 7 and to the posterior wall 8, and two distal walls 11 diverging from each other, connected to the distal end of the wall 10 on the one hand, and to the walls 8 and 9, on the distal side, on the other hand.

The implant 1 also comprises, on its proximal side, relatively to its direction of introduction into the intervertebral space, a hole comprising two coaxial portions 12, 13, i.e. a proximal portion 12 with a larger diameter and a distal portion 13 of smaller diameter, both of these proximal and distal portions 12, 13 being tapped.

Figure 9:
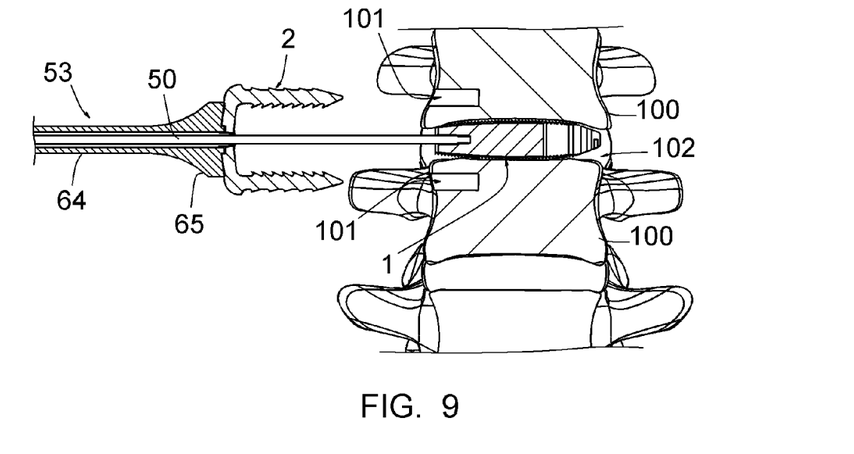
Figure 10:
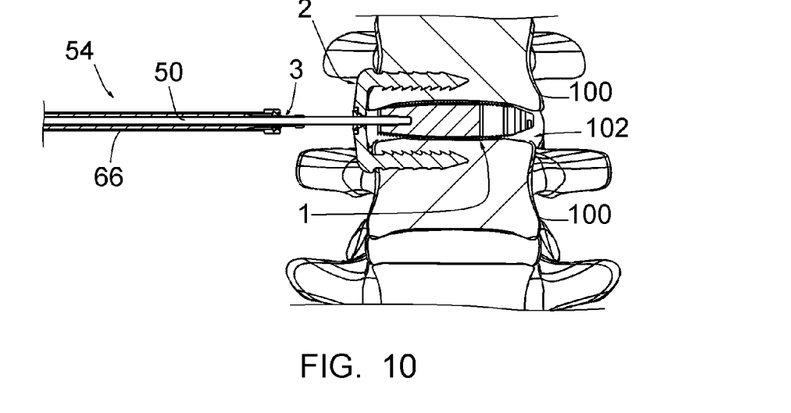
Figure 11:
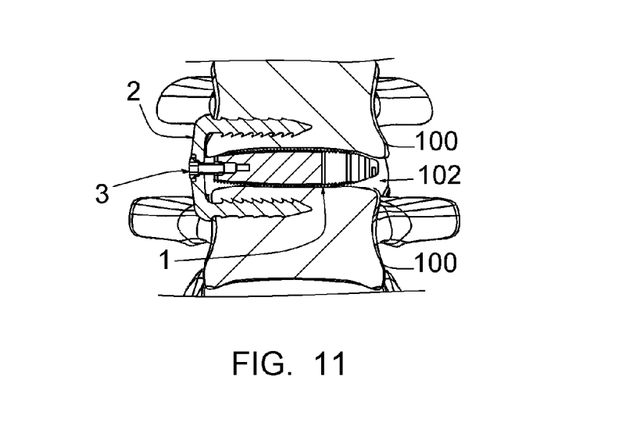

The proximal portion 12 is intended to receive the assembling member 3, screwed into it, as this appears in FIG. 11, and the distal portion 13 is intended to receive, also screwed into it, the distal end portion of a guiding rod 50, see FIGS. 6-10 and 12. The respective diameters of these proximal and distal portions 12, 13 are such that the assembling member 3 may be screwed into the proximal portion 12 while the guiding rod 50 is screwed into the distal portion 13.

The connecting member 2 is in the form of a clamp, comprising a central branch and two jagged side branches intended to be inserted into holes 101 (see FIG. 9) created in the vertebral bodies 100.

Figure 3:
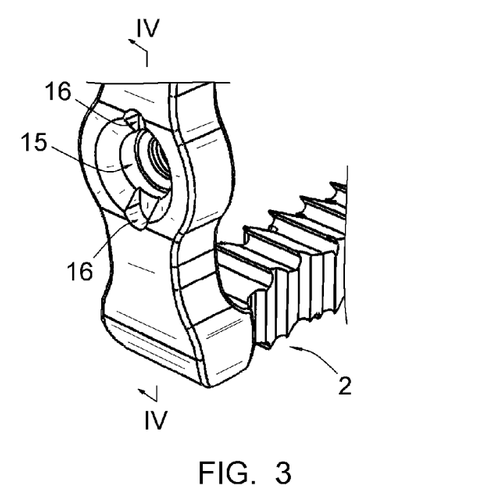
FIG. 3 is a partial view of the connecting member, similar to FIG. 1 at an enlarged scale.
Figure 4:
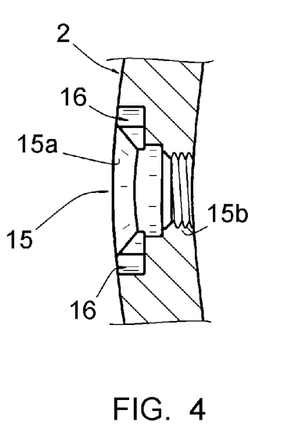
FIG. 4 is a partial view of the connecting member, at an enlarged scale, as a sectional view along the line IV-IV of FIG. 3.

The central branch comprises a middle hole 15 which crosses it, forming as this is shown in FIGS. 3 and 4, a proximal cup 15a and a distal tapped portion 15b. It also comprises two diametrically opposite cavities 16 created from its proximal face.

The assembling member 3 is in the form of a cannulated screw comprising a milled head and a distal threaded portion extending on only one portion of its body. This distal threaded portion is able to be screwed through the portion 15b of the member 2 and into the proximal portion 12 of the hole of the implant 1.

The assembling member 3 has a proximal conformation (cavity) 30 for receiving the end of instrument 54 as shown on FIG. 10 and for being screwed by this instrument 54.

As this appears in FIGS. 10 and 11, the internal conduit of this assembling member 3 is such that the member 3 is able to be fittingly engaged onto the guiding rod 50, with however the possibility of sliding and of rotating; the assembling member 3 may thus be screwed through the distal tapped portion 15b of the connecting member 2 and then into the proximal portion 12 of the hole of the implant 1, allowing the assembling of this member 2 and of the implant 1 to be achieved. In this position, the milled head of the assembling member 3 takes a place in the proximal cup 15a of the hole 15.

The instruments 50-54 comprise said guiding rod 50, said instrument 51 for introducing and impacting the implant 1 into the intervertebral space, said instrument 52 for creating holes in the vertebral bodies 100, said instrument 53 for introducing and impacting the connecting member 2 and said instrument 54 for introducing and placing the assembling member 3.

Figure 6:
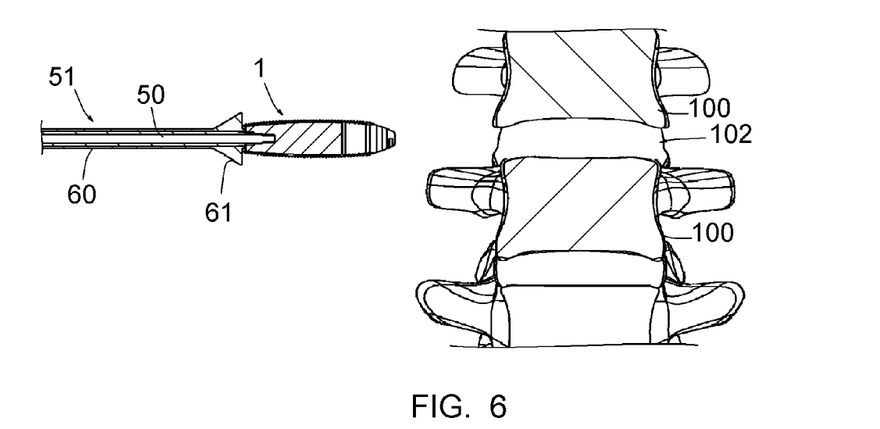
FIGS. 6-11 are front views, with a partial sectional view of the different elements being part of the piece of equipment, during successive steps for placing this piece of equipment on two consecutive vertebrae of a vertebral column.
Figure 12:
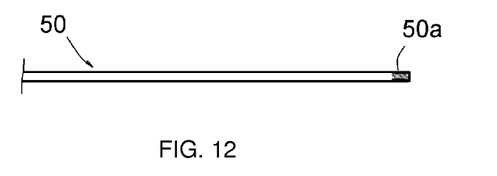
FIG. 12 is a side view of a guiding rod which the equipment comprises.

As shown in FIG. 12, the guiding rod 50 is threaded at an end 50a, so as to be capable to be screwed in said distal portion 13 of the hole of the implant 1, see also FIG. 6.

Figure 7:
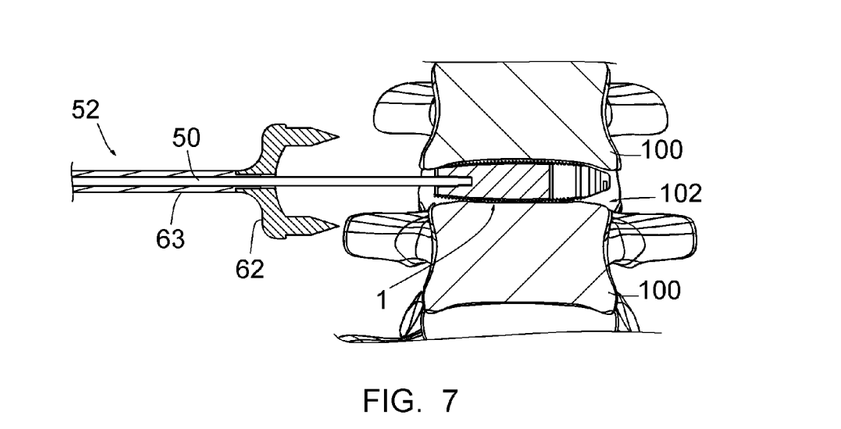
Figure 13:
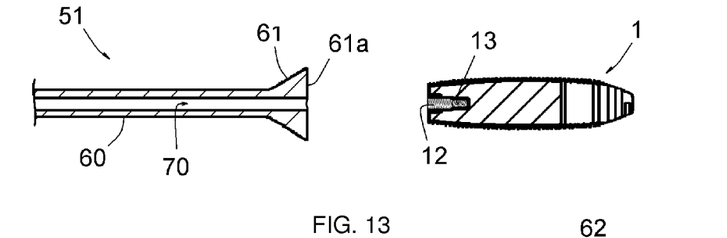
FIG. 13 is, on the left side, a side and sectional view of an instrument for introducing and impacting the implant, and, on the right side, a side and sectional view of the implant along line VII-VII of FIG. 5.
Figure 14:
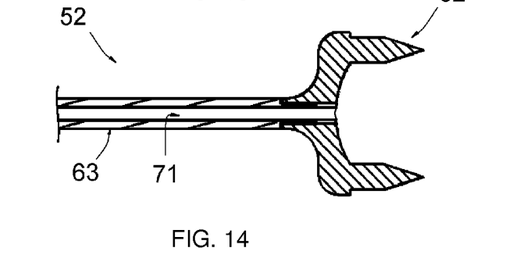
FIG. 14 is a side and sectional view of an instrument for creating holes in vertebral bodies.

As shown in FIGS. 13 and 6, the instrument 51 for introducing and impacting the implant 1 into the intervertebral space 102 comprises a tubular sleeve 60 delimiting a conduit which allows it to be fittingly engaged onto the guiding rod 50 while this rod is connected to the implant 1. This instrument 51 also comprises a flared distal end 61 forming an end face 61a capable of bearing against the implant 1 in this engagement condition in order to allow the introduction and impaction of the implant 1 into the intervertebral space 102. This impaction is made on a proximal portion (not shown) of the instrument 51. In FIGS. 14 and 7, it appears that the instrument 52 for creating holes in the vertebral bodies 100 comprises a head 62 for creating holes, having a shape similar to that of the connecting member 2, and a tubular sleeve 63 fixed to it. The head 62 and the sleeve 63 delimiting a conduit 71 which allows them to be fittingly engaged onto the guiding rod 50 while this rod is connected to the implant 1. This instrument 52 may be slid on this rod 50 until it achieves piercing of the vertebral bodies 100 or enlargement and forming of holes created beforehand in these vertebral bodies 100 (See FIGS. 8 and 9). This piercing or enlargement and forming is made by impaction on a proximal portion (not shown) of the instrument 52.

Figure 15:
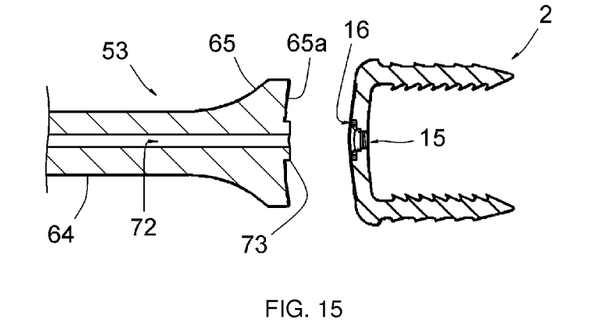
FIG. 15 is, on the left side, a side and sectional view of an instrument for introducing and impacting the connecting member, and, on the right side, a side and sectional view of the connecting member.

As shown in FIGS. 15 and 9, the instrument 53 for introducing and impacting the connecting member as for it comprises (see FIG. 9) a tubular sleeve 64 delimiting a conduit which allows it to be fittingly engaged onto the guiding rod 50 while this rod is connected to the implant 1. This instrument 53 also includes a flared distal end 65 forming and end face 65a capable of bearing against the implant 1 in this engagement condition and two protrusions 73 capable of engaging with the cavities 16 of the member 2 in order to achieve a rotary connection of this instrument 53 and of this member 2 about the axis of the rod 50. The instrument 53 thus in addition to introduction and impaction of the member 2, allows this member 2 to be angularly oriented for the case when this would prove to be necessary in order to bring the side branches of the latter to facing the holes 101 pierced in the vertebral bodies 100. Said impaction is made on a proximal end (not shown) of the instrument 53.

Figure 16:
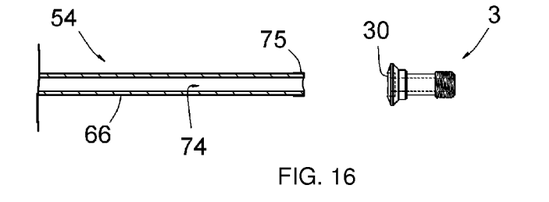
FIG. 16 is, on the left side, a side and sectional view of an instrument for introducing and placing the screw, and, on the right side, a side view of the screw.

The instrument 54 for introducing and placing the assembling member 3, visible in FIGS. 10 and 16, comprises a tubular sleeve 66 delimiting a conduit 74 which allows it to be fittingly engaged onto the guiding rod 50 when this rod is connected to the implant 1 and has a distal conformation 75 which allows it to be rotationally engaged with a proximal conformation 30 of the head of the assembling member 3.

Figure 8:
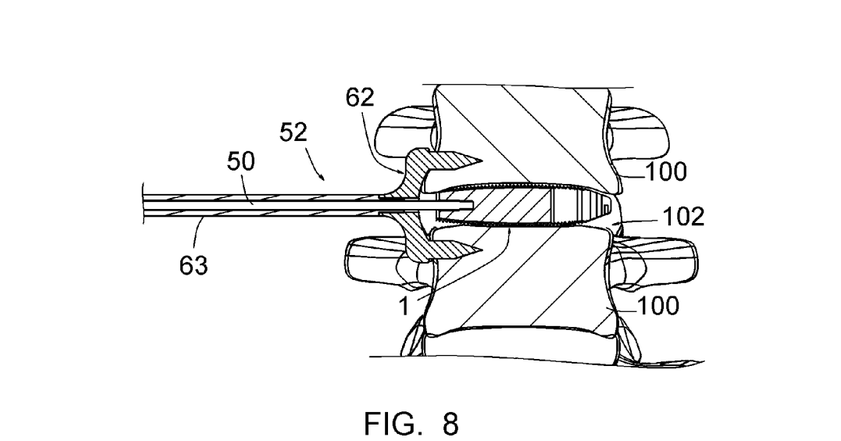

In practice, the procedure for placing the piece of equipment comprises the following steps:

connecting the guiding rod 50 to the implant 1;

engaging onto the guiding rod 50 the introduction and impaction instrument 51 and then introducing and impacting the implant 1 into the intervertebral space 102 (see FIG. 6);

withdrawing the instrument 51;

engaging onto the guiding rod 50 the instrument 52 for creating holes in the vertebral bodies (see FIG. 7) and creating these holes by means of this instrument (see FIG. 8);

withdrawing the instrument 52;

engaging onto the guiding rod 50 the connecting member 2 and the instrument 53 for introducing and impacting this connecting member 2 (see FIG. 9) and placing the connecting member 2 on the vertebral bodies 100;

withdrawing the instrument 53;

engaging onto the guiding rod 50 the assembling member 3 and the instrument 54 for introducing and placing this assembling member 3 (see FIG. 10) and placing the assembling member 3 in the proximal portion 12 of the hole of the implant 1 by means of this instrument;

withdrawing of the instrument 54;

withdrawing the guiding rod 50 (see FIG. 11).

The invention thus provides a piece of vertebral osteosynthesis equipment comprising a guiding rod 50 intended to be connected to the implant 1 as soon as before this implant is placed in the intervertebral space 102 and intended to remain in place on this implant 1 until the end of the placement procedure, this guiding rod 50 not being an obstacle to the placement of the assembling member 3 by means of the two portions 12, 13 of the hole which the implant 1 comprises.

The guiding rod 50 allows the different instruments to be perfectly guided throughout the procedure and to be aligned with the axis of the hole of the implant 1; therefore with it, it is possible to obtain (i) perfect parallelism of the hole 101 created in the vertical bodies 100 with this hole of the implant 1; (ii) perfect coaxiality of the hole 15 of the connecting member 2 with this hole of the implant 1 and (iii) perfect coaxiality of the assembling member 3 with this same hole.

The result is that with the piece of equipment, the assembling of the connecting member 2 with the implant 1 may be achieved under best conditions, and the placement of the assembling member 3 is easy, which allows the use of a narrow and not very invasive approach, in particular a purely lateral approach.

The invention has been described above with reference to an embodiment provided as an example. It is obvious that it is not limited to this embodiment, but that it extends to all the other embodiments covered by the appended claims.

The invention claimed is:

1. A vertebral osteosynthesis equipment comprising:

an intervertebral implant adapted to be introduced into an intervertebral space of two vertebrae, the intervertebral implant including a first side, a second side adapted to be introduced on the intervertebral space, and a hole located on the first side, the hole including a proximal coaxial portion and a distal coaxial portion, the proximal coaxial portion having a first section with a first diameter, the distal coaxial portion having a second section with a second diameter, the first diameter is larger than the second diameter, the proximal and the distal portions comprising respective tapped threads;

a guiding rod having a distal end with a third diameter and a threading on a distal end portion, the third diameter corresponding to the second diameter to secure the distal end portion of the guiding rod to the distal coaxial portion of the hole;

a connecting member to connect both vertebrae, the connecting member connects into the intervertebral implant, the connecting member includes an orifice, the guiding rod passes through the orifice;

an assembling member to connect the connecting member to the intervertebral implant, the assembling member including an internal conduit having an inner diameter and an outer diameter, the inner diameter allows the assembling member to engage and be closely fitted on the guiding rod, and the outer diameter corresponds to the first diameter to secure the assembling member to the proximal portion of the hole;

wherein the distal end of the guiding rod is secured to the hole distal coaxial portion of the hole at the same time that the assembling member is secured to the proximal portion of the hole;

further comprising the following instruments to place the implant, the connecting member and the assembling member onto the vertebrae:

a first instrument for introducing and/or impacting the implant in the intervertebral space, the first instrument comprises a first conduit to be fittingly engaged onto the guiding rod when the guiding rod is connected to the implant, the first conduit comprises a distal end to bear against the implant during the engagement;

a hole creating instrument to create holes in both vertebrae, the hole creating instrument comprising a second conduit to be fittingly engaged on the guiding rod when the guiding rod is connected to the implant;

a second instrument for introducing and/or impacting the connecting member, the second instrument comprising a third conduit to be fittingly engaged onto the guiding rod when the guiding rod is connected to the implant, the third conduit comprises a distal end to bear against the connecting member engaged on the guiding rod during the engagement;

a third instrument for introducing and placing the assembling member, the third instrument comprises a fourth conduit to be fittingly engaged on the guiding rod when the guiding rod is connected to the implant;

the connecting member, the first instrument, the second instrument, and the third instrument engaged with the guiding rod when the guiding rod is connected to the implant.

2. The equipment according to claim 1, wherein the intervertebral implant comprises at least one cavity for receiving a graft.

3. The equipment according to claim 2, wherein the implant further comprises a wall extended through the distal side of the implant and positioned in a middle position relative to an anterior wall and to a posterior wall, the wall diverging into two walls diverging from each other, the at least one cavity is located on the wall.

4. The equipment according to claim 1, wherein the connecting member and the second instrument comprise connecting devices, the connecting device allows the connecting member and the second instrument to bound with each other in rotation about an axis of the orifice of the connecting member- and of the third conduit of the second instrument.

5. The equipment according to claim 4, wherein said connecting member comprises protrusions.

6. The equipment according to claim 1, wherein the orifice of the connecting member comprises a tapped portion through which the assembling member is fastened.

7. A method for placing a vertebral osteosynthesis equipment according to claim 1, the method comprising the steps of:

connecting the guiding rod to the implant;

engaging onto the guiding rod the first instrument and then introducing and/or impacting the implant into the intervertebral space;

withdrawing the first instrument from the intervertebral space;

engaging onto the guiding rod the hole creating instrument in the vertebrae and creating the holes;

withdrawing the hole creating instrument from the vertebrae;

engaging onto the guiding rod the connecting member and the second instrument on the vertebrae;

withdrawing the second instrument from the vertebrae;
engaging onto the guiding rod the assembling member and the third instrument in the proximal portion of the hole of the implant;
withdrawing the third instrument from the intervertebral space; and
withdrawing the guiding rod from the intervertebral space.

\* \* \* \* \*